US006693104B2

(12) United States Patent
Lee et al.

(10) Patent No.: US 6,693,104 B2
(45) Date of Patent: Feb. 17, 2004

(54) THEOBROMINE WITH AN ANTI-CARCINOGENIC ACTIVITY

(75) Inventors: Hyong Joo Lee, Seoul (KR); Ki Won Lee, Suwon (KR); Kyung Sun Kang, Suwon (KR); Dong Young Kim, Kyunggi-do (KR); Hyung Hwan Park, Kyunggi-do (KR); Man Jong Lee, Suwon (KR); Han Soo Kim, Kyunggi-do (KR); Ik Boo Kwon, Seoul (KR)

(73) Assignee: Lotte Confectionery Co., Ltd., Seoul (KR)

( * ) Notice: Subject to any disclaimer, the term of this patent is extended or adjusted under 35 U.S.C. 154(b) by 0 days.

(21) Appl. No.: 10/223,104

(22) Filed: Aug. 15, 2002

(65) Prior Publication Data

US 2003/0099686 A1 May 29, 2003

(30) Foreign Application Priority Data

Oct. 18, 2001 (KR) ........................ 2001-64287

(51) Int. Cl.[7] .............................. A61K 31/52
(52) U.S. Cl. ...................................... 514/263
(58) Field of Search ........................... 514/263

(56) References Cited

U.S. PATENT DOCUMENTS 4,908,212 A 3/1990 Kwon et al.
6,159,451 A 12/2000 Kim et al.

OTHER PUBLICATIONS

Gil et al., Folia Biologica (Prague), (1993), vol. 39, No. 2, pp. 63–68 Abstract Only.*
Bracz et al., Eur. J. Cancer (33, Suppl. 8, S47, 1997) Abstract Only.*
Bracz et al., Oncology Reports, (1998) vol. 5, No. 2, pp. 517–520 Abstract Only.*
Lentini et al., Melanoma Research, (1998 Apr), 8 (2) 131–7 Abstract Only.*
Caragay, A.B., Cancer–Preventive Foods and Ingredients, *Food Technology*, Apr. 1992, pp. 65–68.
Chung, F.L., Inhibition of Lung Carcinogenesis by Black Tea in Fischer Rats Treated with a Tobacco–Specific Carcinogen: Caffeine as an Important Constituent (Abstract), *Cancer Research*, 58, pp. 4096–4101, 1998.
Holder, J.W., Gap Junction Function and Cancer, *Cancer Research*, 53, pp. 3475–3485, 1993.
Huang, M.T., Effects of Tea, Decaffeinated Tea, and Caffeine on UVB Light–Induced Complete Carcinogenesis in SKH–1 Mice; Demonstration of Caffeine as a Biologically Important Constituent of Tea, *Cancer Research*, Jul. 1, 1997, pp. 2523–2629.
Kelloff, G.J. et al., Cancer Chemoprevention: Progress and Promise, *European Journal of Cancer*, vol. 35, pp. 1755–1762.

Lu, Y.P. et al., Inhibitory Effects of Orally Administered Green Tea, Black Tea, and Caffeine on Skin Carcinogenesis in Mice Previously Treated with Ultraviolet B. Light (Abstract), *Cancer Research*, 61, pp. 5002–5009, 2001.
Perchelett, J.P. et al., Effects of 3–Isobutyl–1 Methylxanthine and Cyclic Nucleotides on the Biochemical Processes Linked to Skin Tumor Promotion by 12–O–Tetradecanoylphorbol–13–Acetate, *Cancer Research*, pp. 3927–3935, 1981.
Sporn, M.B., The War on Cancer, *The Lancet*, pp. 1377–1381, 1996.
Surh, Y.J., Molecular Mechanisms of Chemopreventive Effects of Selected Dietary and Medicinal Phenolic Substances, *Mutation Research*, 428, pp. 305–327, 1999.
Takahashi, M et al., Combined Effect of CDDP and Caffeine Against Human Gastric Cell Lint in Vivo (Abstract), *Anticancer Research*, pp. 4399–4401, 1998.
Theiss, J.C., Inhibiting Effect of Caffeine on Spontaneous and Urethan–Induced Lung Tumors in Strain A Mice, *Cancer Research*, pp. 1757–1761, 1978.
Upham, B.L. et al., Hydrogen Peroxide Inhibits Gap Junctional Intercellular Communication in Glutathione Sufficient But Not Glutathione Deficient Cells, *Carcinogenesis*, 18, pp. 37–42, 1997.
Yamasaki, H., Gap Junctional Intercellular Communication and Carcinogenesis, *Carcinogenesis*, pp. 1051–1058, 1990.
Yang, C.S., Mechanisms of Inhibition of Carcinogenesis by Tea, *BioFactors*, 13, pp. 73–79, 2000.
Zoumas, B.L. et al., Theobromine and Caffeine Content of Chocolate Products, *Journal of Food Science*, 45, pp. 314–316, 1980.
Zoumas, B.L. et al., Theobromine and Caffeine Content of Chocolate Products, *Journal of Food Science*, 45, pp. 314–316, 1980.
Gil et al., Effect of Puringeric Receptor Antagnonists Suramin and Theobromine on Tumor–Induced Angiogenesis in BALB/c Mice, *Folia Biologica (Praha)*, vol. 39, p. 63–68, 1993.
Barcz et al., The Influence of Theobromine on Angiogenic Activity and Proangiogenic Cytokines Production of Human Ovarian Cancer Cells, *Oncology Reports* 5, pp. 517–520, 1998.
Barcz et al., The Influence of Theobromine on Angiogenic Activity of Human Ovarian Cancer Cells, *The European Journal of Cancer*, p. S47, vol. 33, Supp. 8, 1997.
Lentini, A. et al., Inhibition of Melanoma Pulmonary Metasisis by Methylxanthines Due to Decreased Invasion and Proliferation, *Melanoma Research*, vol. 8, pp. 131–137, 1998.

* cited by examiner

*Primary Examiner*—Jerome D. Goldberg
(74) *Attorney, Agent, or Firm*—Pennie & Edmonds LLP

(57) ABSTRACT

Disclosed is theobromine with an anti-carcinogenic activity which inhibits the suppression of GJIC (gap junctional intercellular communication), a pathological phenomenon occurring during development of various kinds of cancers including liver cancer, as well as DNA synthesis of cancer cells thereby inhibiting proliferation of liver, gastric and colon cancer cells.

3 Claims, 3 Drawing Sheets a    b    c

THEOBROMINE WITH AN ANTI-CARCINOGENIC ACTIVITY

FIELD OF THE INVENTION

The present invention relates to theobromine with an anti-carcinogenic activity, and more particularly, to theobromine which inhibits the suppression of gap junctional intercellular communication (GJIC), a pathological phenomenon occurring during development of various kinds of cancers including liver cancer, as well as DNA synthesis of cancer cells thereby inhibiting proliferation of cancer cells.

BACKGROUND OF THE INVENTION

Although a wide range of attempts has been made to treat cancer over the last three decades, incidence and death rates of cancer have not decreased. (Sporn, M. B., *Lancet*, 347:1377–1381, 1996) This appears mainly due to the fact that the approaches on cancers for the past thirty years have been mostly focused on from the therapeutic point rather than preventive point. As is already known, intake of certain food or a drug that contains components which can effectively inhibit or delay the multi-step progress of cancer will help to reduce the risk of cancer and the subsequent mortalities resulted thereof and many researches have been carried out (Kang et al., *Chemoprevention of cancer*, Korea Medicine, 2000; Surh, Y. J., *Mutat. Res*, 428:305–327, 1999; Sporn, M. B., *Lancet*, 347:1377–1381, 1996; Caragay, A. B., *Food Technol.*, 65–68, 1992).

Carcinogenesis is a multi-step process comprising stages of initiation, promotion and progression. In searching of agents which may be effective in prevention or inhibition of cancer, the recent researches have been more concerned with identifying substances that can inhibit promotion and promotion stages rather than those of initiation stage, which is a relatively short and irreversible stage (Kang et al., *Chemoprevention of cancer*, Korea Medicine, 2000; Surh, Y. J., *Mutat. Res,* 428: 305–327, 1999; Sporn, M. B., *Lancet*, 347: 1377–1381, 1996). In particular, unlike pharmaceutical drugs, the prevention and inhibition of cancer by means of food extract and fraction will become more effective if they target on the promotion stage of carcinogenesis, which is generally progressed for more than 20 years and is also reversible (Kang et al., *Chemoprevention of cancer*, Korea Medicine, 135–136, 2000; Yamasaki, H. et al, *Carcinogenesis* 11: 1051–1058, 1999; Kelloff. G. J. et al., *Eur. J. Cancer,* 35: 1755–1762, 1999; Surh, Y. J., *Mutat. Res,* 428: 305–327, 1999).

Gap junctional intercellular communication (GJIC) is essential for maintaining the homeostatic balance through modulating cell proliferation and differentiation in multicellular organisms. Inhibition of GJIC is considered as a key biochemical index observed at carcinogenesis, particularly to tumor promotion stage; therefore, substances that can inhibit such a process is expected to inhibit the promotion stage of carcinogenesis thereby preventing as well as inhibiting the development of cancer. Further, proliferation of cancer cells by DNA synthesis is considered as a key biological index observed at the progression stage of carcinogenesis; therefore, substances that can inhibit such a process is expected to inhibit the progression stage of carcinogenesis thereby preventing as well as inhibiting the development of cancer (Kang et al., *Chemoprevention of cancer*, Korea Medicine, 135–136, 2000; Yamasaki, H. et al, *Carcinogenesis* 11:1051–1058, 1990; Kelloff. G. J. et al., *Eur. J. Cancer,* 35:1755–1762, 1999; Surh, Y. J., *Mutat. Res,* 428: 305–327, 1999; Holder. J. W. et al., *Cancer Res.,* 53:3475–3485, 1993).

A variety of foods such as coffee, tea, coke and chocolate contain caffeine, a xanthine derivative (Lee, W. J., *Pharmacology Lecture*, Medical culture, 195–198, 1993). In particular, theobromine, also a xanthine derivative, is abundant in cacao bean or cacao bean husk unlike caffeine. In general, cacao bean contains about 1.5–3% of theobromine and cacao bean husk contains about 2% of theobromine. Processed food such as chocolate, which is made from cacao bean, contains about 0.2–0.5% of theobromine and this content is about 7–10 times larger than that of caffeine (Barry, L. Z. et al., *J. Food Sci.,* 45:314–316, 1980). General pharmacological functions of xanthine derivatives are stimulation of central nervous system, skeletal muscle and cardiac muscle as well as relaxation of smooth muscle and coronary artery, accentuation of secretion of gastric juice, and diuresis. However, the pharmacological activity of theobromine is known to be much weaker than that of caffeine (Lee, W. J., *Pharmacology Lecture*, Medical culture, 195–198, 1993). By contrast, caffeine is present in a variety of foods and has a wide scope of pharmacological activities, theobromine is only abundantly present in cacao bean and cacao bean husk and thus the studies on theobromine has not been extensively carried out. Caffeine has been reported to have an anti-carcinogenic activities; for example, a synergistic effect on therapeutic agent for gastric cancer (Takahashi, M. et al., *Anticancer Res.* 18:4399–4402, 1998), an inhibitory effect on lung cancer (Jeffrey, C. et al., *Cancer Res.* 38:1757–1761, 1978; Chung, F. L. et al., *Cancer Res.,* 58:4096–4101, 1998), and an inhibitory effect on TPA (12-O-tetradecanoyphorbol-13-acetate)-induced carcinogenesis (Perchellet, J. P. et al., *Cancer Res.* 41:3927–3925, 1981). In the preventive role of green tea and black tea, caffeine has been also reported to play an important role in parallel with polyphenol (Yang. C. S., *Biofactor* 13:73–79, 1999; Huang, M. T. et al., *Cancer Res.* 57: 2623–2629, 1997; Lu, Y. P. et al., *Cancer Res.,* 61: 5002–5009, 2001).

However, there have been no studies revealed on the effect of theobromine contained in cacao bean and cacao bean husk with respect to prevention and inhibition of cancers. In particular, there has been no report on the effect of theobromine on cancers the developmental rates of which are relatively high in Asians as well as Koreans such as liver cancer, gastric cancer and colon cancer.

SUMMARY OF THE INVENTION

The inventors of the present invention, while searching for a promising candidate for an anti-carcinogenic agent among natural foods for safety reason, discovered that theobromine, which is abundantly present in cacao bean and cacao bean husk, has an anti-carcinogenic activity such as inhibiting the suppression of GJIC and DNA synthesis of cancer cells, which are characteristic pathological phenomena occurring during promotion and progression stages of carcinogenesis.

Therefore, the object of the present invention is to provide an anti-carcinogenic agent comprising theobromine as an active ingredient.

DETAILED DESCRIPTION OF THE INVENTION

Figure 1:
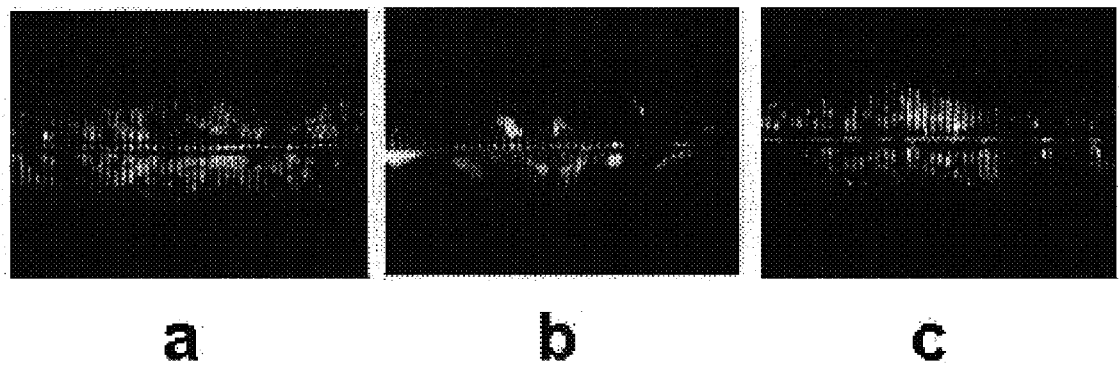
FIG. 1 is a set of pictures that show inhibitory effect of theobromine against suppression of GJIC generated by $H_2O_2$, a cancer promoter and one of the strongest reactive oxygen species (ROS) in human body, in rat liver epithelial cells (a: a untreated control group; b: a group treated with 400 μM H₂O₂, c: a group treated with both 200 μM theobromine and 400 μM H₂O₂).

The present invention relates to an anti-carcinogenic agent comprising theobromine of the following formula 1 as an active ingredient.

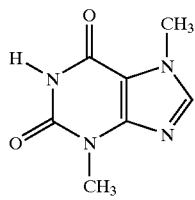

(1)

The present invention is described in more detail as set forth hereunder.

The theobromine of the present invention is useful in prevention as well as inhibition of carcinogenesis by not only inhibiting DNA synthesis of cancer cells but also inhibiting the suppression of GJIC, which are characteristic phenomena occurring during the promotion and progression stages of carcinogenesis. Therefore, the present invention also relates to a pharmaceutical drug or a food additive that comprises theobromine as an active ingredient.

The process of isolating theobromine from cacao bean or cacao bean husk is as follows.

First, cocoa butter is removed from dried cacao bean and to 1 part by wt of the remaining cacao bean fraction (cacao mass) or cacao bean husk is added with 4–10 parts by wt of aqueous solution of 50% acetone, 50% ethanol or 50% methanol (Duksan Co., Ltd., Korea). Then, agitation extraction is performed for the mixture while refluxing for 4–6 hr at 40–70° C. Supernatant is recovered after centrifugation of the resulting extract, and the remaining mass is further extracted by repetition. The extract above is combined, dried, filtered and the extract of cacao bean or cacao bean husk is obtained. Finally, theobromine is isolated from the extract by HPLC according to Kreiser's method (Barry, L. Z. et al., *J. Food Sci.*, 45:314–316, 1980). Thus obtained theobromine or chemically synthesized theobromine was examined on inhibitory effects on suppression of GJIC and proliferation of cancer cells and we found that they inhibit the suppression of GJIC and proliferation of cancer cells occurring at promotion and progression stages of carcinogenesis.

The present invention also relates to a pharmaceutical drug or a food additive comprising theobromine as an active ingredient and they are prepared according to a known manufacturing method.

In manufacturing pharmaceutical drugs comprising theobromine, theobromine can be prepared by theobromine itself or they can be prepared in the form of powder, granules, capsules and injections by combining theobromine with a pharmaceutically acceptable carrier, a forming agent, a diluent and the like. Further, the level of theobromine administration can vary according to rate of body absorption, body weight, age, sex and health state of a patient, diet, time and method of administration, excretion rate, seriousness of an illness, and the like, and it is generally preferred to administer 0.1–5 mg/kg of body weight. Therefore, the pharmaceutical drugs comprising theobromine of the present invention should be manufactured considering its effective range. Thus manufactured unit preparations for administration can be administered according to a specialized medication under the supervision of a specialist or by a patient's request or a few times at regular intervals of time.

As described above, the pharmaceutical drugs or food additives comprising theobromine as an active ingredient have excellent effect on the inhibition and prevention of carcinogenesis.

Hereunder is given a detailed description of the present invention using the following Examples, however, it should not be construed as limiting the scope of the present invention.

REFERENCE EXAMPLE 1

Isolation of Theobromine from Cacao Bean

Cocoa butter was removed from cacao bean containing cacao bean husk, 6 parts by wt of 50% acetone solution (Duksan Co., Ltd., Korea) was added to 1 part by wt of the remaining fraction (cacao mass) and agitation extraction was performed for 5 hr at 60° C. while refluxing. The extract was centrifuged for 30 min at 4° C. at the rate of 8,000 rpm (Vision Co., Ltd., Korea) and the resulting supernatant was collected. Extraction was repeated once for the remnant and all the supernatant was combined. Theobromine was isolated from the extract by HPLC according to Kreiser's method.

REFERENCE EXAMPLE 2

Isolation of Theobromine from Cacao Bean Husk

Theobromine was isolated using the same method in the above Reference Example 1 with the exception that cacao bean husk was used instead of cacao bean.

REFERENCE EXAMPLE 3

Use of Synthesized Theobromine

Theobromine was purchased from Sigma Co., Ltd. (USA) and used accordingly.

The inhibitory effects of theobromine, both isolated and synthesized according to the present invention on the suppression of GJIC and the hyperphosphorylation (P3) of Cx43 by H₂O₂ and on proliferation of cancer cells of liver cancer, gastric cancer and colon cancer were examined.

EXAMPLE 1

Inhibitory Effect of Theobromine on the Suppression of GJIC

H₂O₂, a cancer promoter and one of the strongest ROS in human body, induces the suppression of gap junction channel via hyperphosphorylation of connexin43 proteins (Cx43) which mainly modulate GJIC. The effect of theobromine on the suppression of GJIC and on the hyperphosphorylation of connexin43 by $H_2O_2$ were examined.

1-1. Inhibitory Effect of Theobromine on the Suppression of Gap Junction Channel by $H_2O_2$ The effect of theobromine on the suppression of gap junction channel induced by $H_2O_2$ was examined according to a known method of Scrape Loading/Dye Transfer (SL/DT) assay (Upham, B. L., Kang, K. S., Cho, H. Y., & Trosko, J. E., *Carcinogenesis*, 18: 37–42, 1997), as further explained below.

WB-F344 cells were used as a liver cell in order to examine its inhibitory effect on the suppression of gap junction channel in liver cells. The above liver cells were cultured in a MEM-media with 10% FBS, added with 100 IU/mL of penicillin and 100 μg/mL of streptomycin, in an incubator at 37° C. with 5% $CO_2$ (Forma Scientific Co., Marjetta, Ohio, USA). The media compositions used in the above culture were purchased from GIBCO BRL (Grand Island, N.Y., USA). Thus cultured liver cells in media were transferred to each 2 mL petri dish ($1 \times 10^5$ cells/mL) and cultured for 44 hr. Then the above culturing media were replaced with fresh media with various concentrations of theobromine while the control group was also replaced with fresh media only. Four hours after that, the media were treated theobromine with various concentrations 400 μM by $H_2O_2$ together while the control group was replaced with fresh medial. One hour after the above treatment, the inhibitory level of theobromine on the suppression of gap junction channel by $H_2O_2$ was observed by means of a confocal microscope (BioRad, Hercules, Calif., USA) using Lucifer Yellow dyeing. As shown in FIG. 1, treatment with 200 μM of theobromine completely inhibit the suppression of gap junction channel by by $H_2O_2$ compared with treated with $H_2O_2$ only.

1-2. Inhibitory Effect of Theobromine on the Hyperphosphorylation of Connexin43 by $H_2O_2$ $H_2O_2$, a cancer promoter and one of the strongest ROS in human body, induces the suppression of gap junction channel by hyperphosphorylation of connexin43 proteins (Cx43) which mainly modulate GJIC. The inhibitory effect of theobromine on the hyperphosphorylation of connexin43 was examined by using a western blot analysis (Upham, B. L., Kang, K. S., Cho, H. Y., & Trosko, J. E. *Carcinogenesis* 18: 37–42, 1997).

Protein was extracted from cells cultured the same as in the above 1-1 by using 20% SDS which contains 1 mM phenylmethylsulfonylfluoride (PMSF). Protein content was measured using a DC assay kit (Bio-Rad Corp., Richmond, Calif., USA). About 15 μg each of the extracted proteins was loaded on a 12.5% SDS-PAGE gel and separated by gel electrophoresis. Connexin43 was detected by using an ECL kit (Amersham, Life Science, Denver, USA) after reacting with a monoclonal body (Zymed, South San Francisco, Calif., USA).

Figure 2:
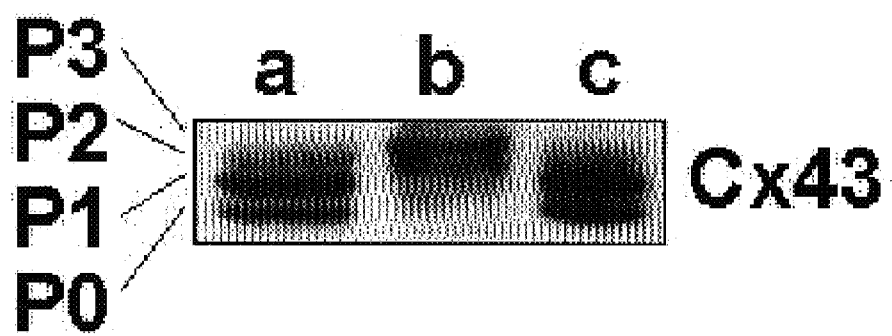
FIG. 2 is a picture that shows inhibitory effect of theobromine against hyperphosphorylation of connexin 43, a major protein that controls GJIC, generated by H₂O₂ in rat liver epithelial cells (a: a control group; b: a group treated with 400 μM H₂O₂, c: a group treated with both 200 μM theobromine and 400 μM H₂O₂).

As shown in FIG. 2, theobromine inhibited the hyperphosphorylation of connexin43 by $H_2O_2$. As shown in FIGS. 1 and 2, theobromine was shown to have an anticarcinogenic effect by inhibiting the suppression of GJIC.

EXAMPLE 2

Inhibitory Effect of Theobromine on Proliferation (DNA Synthesis) of Liver Cancer Cells The inhibitory effect of theobromine on the proliferation of liver cancer cells was examined by using $^3H$ thymidine uptake assay (Marshall, E. S. et al. *European J. Cancer*, 30A: 1370–1376, 1994).

HepG2 was used as liver cancer cells. The HepG2 liver cancer cells were cultured in RPMI-1640 media with 10% FBS, 100 IU/mL of penicillin and 100 μg/mL of streptomycin, in a 37° C. incubator with 5% $CO_2$ (Forma Scientific Co., Marjetta, Ohio, USA). The media were purchased from GIBCO BRL (Grand Island, N.Y., USA). Thus cultured HepG2 liver cancer cells were transferred to 96 well plates, each of which contains $2 \times 10^4$ cells and were added with various concentrations of theobromine obtained from the reference examples 1–3 and were cultured for 72 hr. Six hours prior to recovery of the above cells, each well was added with 1 μCi of $^3H$-Thymidine (Sigma, St. Louis, Mo., USA). After completion of the culture, the cells were recovered into a glass fiber filter (Brandel Inc., Gaithersburg, Mass., USA) by using a recovery instrument (Cambridge Scientific Inc., Cambridge, Mass., USA). The incorporation of $^3H$-thymidine of recovered cells after combining with 3 mL of scintillation cocktail solution (Wallac, Turku, Finland) was examined in a liquid scintillation counter (Wallac, Turku, Finland). The whole process was repeated three times according to the above method.

Figure 3:
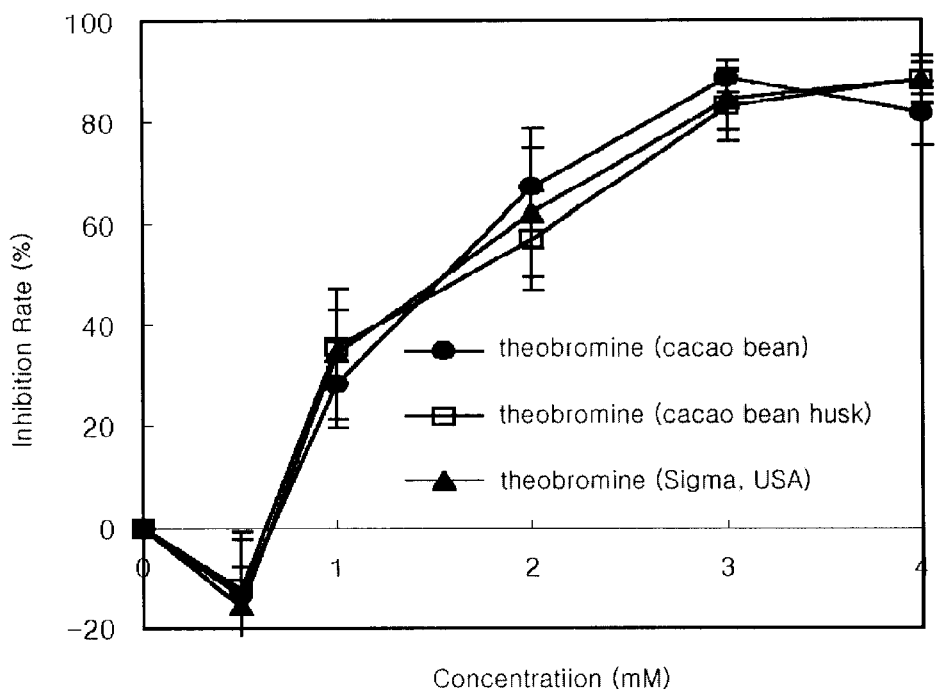
FIG. 3 is a graph that shows inhibitory effect of theobromine on the proliferation via inhibition of DNA synthesis of HepG2, a liver cancer cell.

As shown in FIG. 3, the inhibition rate of DNA synthesis of liver cancer cells treated with theobromine was increased in a dose-dependent manner, which shows that inhibition of proliferation of liver cancer cells is dependent on the concentration of theobromine.

EXAMPLE 3

Figure 4:
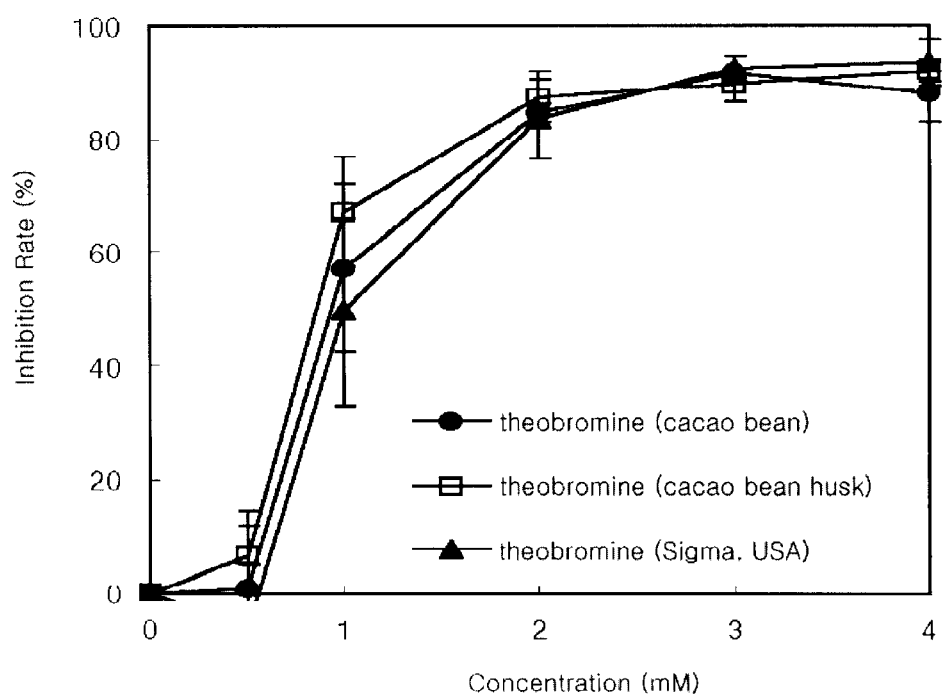
FIG. 4 is a graph that shows inhibitory effect of theobromine on the proliferation via inhibition of DNA synthesis of SNU1, a gastric cancer cell.

Inhibitory Effect of Theobromine on Proliferation (DNA Synthesis) of Gastric Cancer Cells Gastric cancer cell SNU1 was treated with various concentrations of theobromine the same as in the Example 2 and the result is shown in FIG. 4. As shown in FIG. 4, the inhibition rate of DNA synthesis of gastric cancer cells treated with theobromine was increased in a dose-dependent manner, which shows that inhibition of proliferation of gastric cancer cells is dependent on the concentration of theobromine.

EXAMPLE 4

Figure 5:
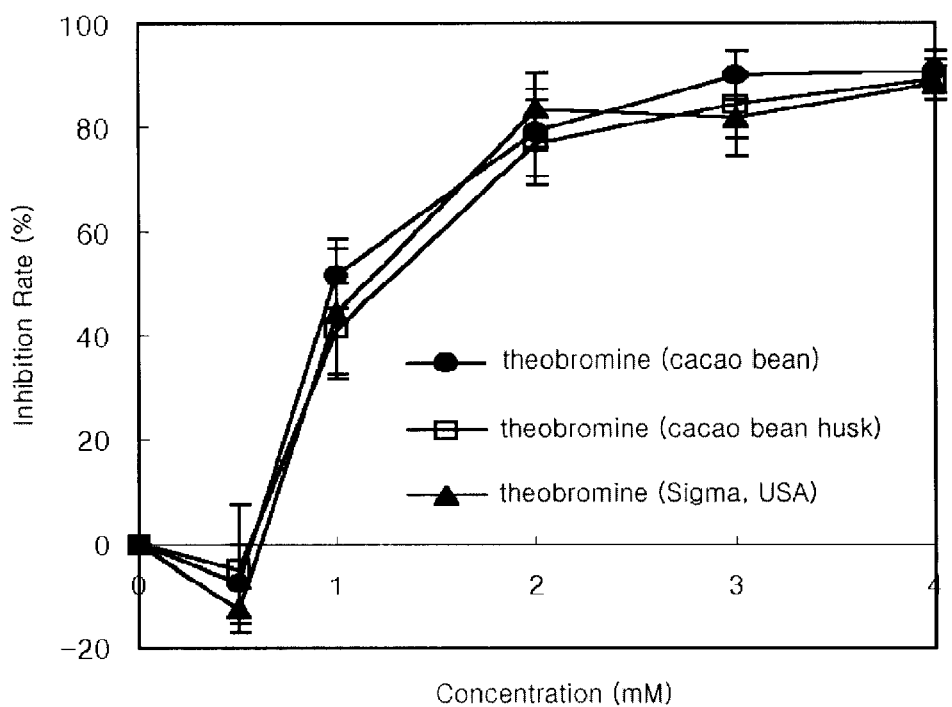
FIG. 5 is a graph that shows inhibitory effect of theobromine on the proliferation via inhibition of DNA synthesis of SNUC2A, a colon cancer cell.

Inhibitory Effect of Theobromine on Proliferation (DNA Synthesis) of Colon Cancer Cells Colon cancer cell SNUC2A was treated with various concentrations of theobromine the same as in the Example 2 and the result is shown in FIG. 5. As shown in FIG. 5, the inhibition rate of DNA synthesis of colon cancer cells treated with theobromine was increased in a dose-dependent manner, which shows that inhibition of proliferation of colon cancer cells are dependent on the concentration of theobromine.

Therefore, it was shown from the above examples that theobromine increases GJIC, inhibits DNA synthesis of liver cancer cells, gastric cancer cells, and colon cancer cells, which shows that theobromine has preventive and inhibitory effects in carcinogenesis.

EXAMPLE 5

Manufacture of Tablets

| | |
|---|---|
| Active ingredient | 10 g |
| Lactose | 70 g |
| Crystalline cellulose | 15 g |
| Magnesium stearate | 5 g |
| Total | 100 g |

The above ingredients were crushed into small pieces and manufactured into tablets by a direct tableting method. Each tablet contains a total of 100 mg, of which the amount of active ingredient accounts for 10 mg.

EXAMPLE 6

Manufacture of Powder Preparation

| | |
|---|---|
| Active ingredient | 5 g |
| Corn strach | 55 g |
| Carboxy cellulose | 40 g |
| Total | 100 g |

The above ingredients were crushed into small pieces and manufactured into powder. One hundred mg of thus prepared powder was added into a soft capsule and manufactured capsule preparations.

EXAMPLE 7

Toxicity Test

The toxicity of theobromine of the present invention was performed as follows. Theobromine, which was dissolved in dimethylsulfoxide (DMSO) and diluted in water, was administered to rat (10 mice/group) at the concentration of 0.5 g/kg and mice were observed for 7 days. The result revealed that all mice survived.

EXAMPLE 8

Chewing gums were manufactured by means of a conventional method by using a composition comprising 20 wt % of gum base, 76.9 wt % of sugar, 1 wt % of flavor, 2 wt % of water and 0.1 wt % of theobromine.

EXAMPLE 9

Candies were manufactured by means of a conventional method by using a composition comprising 60 wt % of sugar, 39.8 wt % of starch syrup, 0.1 wt % of flavor and 0.1 wt % of theobromine.

EXAMPLE 10

Chewing gums were manufactured by means of a conventional method by using a composition comprising 50 wt % of sugar alcohol, 49.8 wt % of maltose, 0.1 wt % of flavor and 0.1 wt % of theobromine.

EXAMPLE 11

Biscuits were manufactured by means of a conventional method by using a composition comprising 25.59 wt % of first grade weak flour, 22.22 wt % of first grade medium flour, 4.80 wt % of sugar, 0.73 wt % of salt, 0.78 wt % of glucose, 11.78 wt % of palm shortening, 1.54 wt % of ammonium bicarbonate, 0.17 wt % of sodium bicarbonate, 0.16 wt % of sodium metabisulfite, 1.45 wt % of rice flour, 0.0001 wt % of vitamin $B_1$, 0.0001 wt % of vitamin $B_2$, 0.04 wt % of milk flavor, 20.6998 wt % of water, 1.16 wt % of whole milk powder, 0.29 wt % of dried milk replacer, 0.03 wt % of calcium diphosphate, 0.29 wt % of spray salt, 7.27 wt % of spray milk and 1 wt % of theobromine.

EXAMPLE 12

Drinks were manufactured by means of a conventional method by using a composition comprising 0.26 wt % of honey, 0.0002 wt % of thioctic acid amide, 0.0004 wt % of nicotinic acid amide, 0.0001 wt % of riboflavin 5'-phosphate sodium, 0.0001 wt % of pyridoxine HCl, 0.001 wt % of inositol, 0.002 wt % of ortho acid, 98.7362 wt % of water, and 1 wt % of theobromine.

EXAMPLE 13

Drinks were manufactured by means of a conventional method by using a composition comprising 3.5 wt % of fruit extract, 4.8 wt % of fruit puree, 7.78 wt % of sugar, 0.11 wt % of citric acid, 82.71 wt % of purified water, and 1 wt % of theobromine.

EXAMPLE 14

Sausages were manufactured by means of a conventional method by using a composition comprising 65.18 wt % of pork, 25 wt % of chicken, 3.5 wt % of starch, 1.7 wt % of soybean protein, 1.62 wt % of salt, 0.5 wt % of glucose, 1.5 wt % of glycerine, and 1 wt % of theobromine.

EXAMPLE 15

Tablet-type of supplementary health food was manufactured by means of a conventional method by using a composition comprising 55 wt % of spirurina, 10 wt % of enzymetic degradation product of guar gum, 0.01 wt % of vitamin $B_1$ hydrochloride, 0.01 wt % of vitamin $B_6$ hydrochloride, 0.23 wt % of DL-methionine, 0.7 wt % of magnesium stearate, 22.2 wt % of lactose, 1.85 wt % of corn starch, and 10 wt % of theobromine.

EXAMPLE 16

Capsule-type of supplementary health food was manufactured by means of a conventional method by using a composition comprising 11.26 wt % of chitooligosaccharide, 0.2 wt % of garlic powder, 0.2 wt % of ginkgo extract powder, 0.9 wt % of β-carotene (30% suspension), 1.2 wt % of α-tocopherol, 1.2 wt % of lecithin, 4.5 wt % of refined palm oil, 1.6 wt % of yellow beeswax, 18.994 wt % of soybean oil, 37.83 wt % of gelatin, 16.51 wt % of glycerine, 0.09 wt % of ethylvanilline, 0.076 wt % of titanium dioxide, 0.44 wt % of food color, and 10 wt % of theobromine.

As described in the above, theobromine of the present invention showed that it inhibits GJIC suppression as well as proliferation of cancer cells, major pathological phenomena occurring at promotion and progression stages of carcinogenesis, thereby inhibiting development of cancer. The theobromine preparation manufactured according to the present invention can be regarded as a food equivalent and thus can be safely administered without additional purification step. Further, the process of manufacturing theobromine preparation by a simple isolation enables to reduce unit cost of production as compared to conventional anti-carcinogenic agents and also the recycling of huge amount of cacao bean husk, which used to be discarded, can be valued much from the economic point of view.

What is claimed is:

1. A method of inhibiting carcinongenesis associated with colon cancer, gastric cancer or liver cancer which comprises orally administering to a human patient in need thereof 0.1–5 mg of theobromine per kg body weight of the patient.

2. The method according to claim 1 wherein the theobromine is administered orally in a tablet or capsule form.

3. The method according to claim 1 wherein the theobromine is administered in a food additive selected from the group consisting of chewing gum, biscuit, bread, cake, cracker, cookie, sausage, beverage, and health-improving food.

* * * * *